US 7,749,202 B2

(12) United States Patent
Miller et al.

(10) Patent No.: US 7,749,202 B2
(45) Date of Patent: Jul. 6, 2010

(54) DUAL MATERIAL PLUNGER TIP FOR USE WITH A SYRINGE

(75) Inventors: Timothy M. Miller, Phoenixville, PA (US); Neil Strausbaugh, Montgomery, PA (US); John R. Wolfe, Selinsgrove, PA (US); Anthony L. Eaton, Watsontown, PA (US)

(73) Assignee: West Pharmaceutical Services, Inc., Lionville, PA (US)

( * ) Notice: Subject to any disclaimer, the term of this patent is extended or adjusted under 35 U.S.C. 154(b) by 284 days.

(21) Appl. No.: 11/468,199

(22) Filed: Aug. 29, 2006

(65) Prior Publication Data

US 2007/0060896 A1    Mar. 15, 2007

Related U.S. Application Data

(60) Provisional application No. 60/712,324, filed on Aug. 29, 2005.

(51) Int. Cl.
*A61M 5/315* (2006.01)
*A61M 5/00* (2006.01)

(52) U.S. Cl. .................. 604/222; 604/218; 604/181

(58) Field of Classification Search ................ 604/218, 604/222, 225, 228, 230; D24/112; 206/571, 206/365
See application file for complete search history.

(56) References Cited

U.S. PATENT DOCUMENTS 3,577,980 A * 5/1971 Cohen ...................... 600/578
4,704,105 A * 11/1987 Adorjan et al. ............. 604/222
4,710,170 A    12/1987 Haber et al.
5,009,646 A *  4/1991 Sudo et al. .................. 604/230
5,314,415 A *  5/1994 Liebert et al. ............... 604/218
5,314,416 A *  5/1994 Lewis et al. ................. 604/219
5,395,326 A    3/1995 Haber et al.
5,409,465 A *  4/1995 Boggs et al. ................ 604/191
5,411,488 A    5/1995 Pagay et al.
5,865,803 A *  2/1999 Major ......................... 604/122
5,980,487 A * 11/1999 Jones et al. .................. 604/110
6,004,300 A * 12/1999 Butcher et al. .............. 604/222
6,017,330 A *  1/2000 Hitchins et al. ............. 604/218
6,224,577 B1 * 5/2001 Dedola et al. ............... 604/218
6,334,553 B1 * 1/2002 Bouras et al. ............... 222/386
6,511,459 B1 * 1/2003 Fago .......................... 604/181
2003/0233075 A1 * 12/2003 Huegli ........................ 604/222

FOREIGN PATENT DOCUMENTS

EP    0965354    12/1999
FR    2547201    12/1984

OTHER PUBLICATIONS

Int'l Search Report Issued Mar. 27, 2007 in Int'l Application No. PCT/US2006/033493.

* cited by examiner

*Primary Examiner*—Nicholas D Lucchesi
*Assistant Examiner*—Ian K Holloway
(74) *Attorney, Agent, or Firm*—Panitch Schwarze Belisario & Nadel LLP

(57) ABSTRACT

A plunger tip for being located on a distal end of a syringe plunger and for sliding sealed engagement with an interior surface of a syringe barrel includes a core constructed of a generally rigid material. The core has a first end for being secured to the plunger, a second end and an endless sidewall between the first and second ends. An elastomeric sleeve at least partially surrounds the endless sidewall of the core.

12 Claims, 11 Drawing Sheets

DUAL MATERIAL PLUNGER TIP FOR USE WITH A SYRINGE

CROSS-REFERENCE TO RELATED APPLICATIONS

This application claims the benefit of U.S. Provisional Patent Application No. 60/712,324 filed Aug. 29, 2005 entitled "Dual Material Plunger Tip for Use with a Syringe" and is incorporated by reference herein in its entirety.

BACKGROUND OF THE INVENTION

This invention generally relates to plunger tips for syringes and, more particularly, to a dual material plunger tip having a solid core for use with a syringe.

Typically, syringes have plunger tips that are made entirely from a single elastomeric material. Such elastomeric plunger tips may tend to interact with the contents of the syringe, leading to breakdown of the plunger tip and contamination of the syringe contents. Additionally, there is a tendency for elastomeric plunger tips, when left in one position for an extended period of time, to "set" in that position. That is, the elastomeric plunger tip sticks to an inner wall of the syringe barrel, such that an increased force is required to break the adhesion between the plunger tip and the inner wall and begin movement of the plunger tip within the syringe barrel. Also, because of the flexible nature of elastomeric plunger tips, the mechanical connection between the plunger and the plunger tip may tend to be relatively unstable, such that the plunger can move with respect to the plunger tip. Such movement can potentially cause the misalignment of the plunger and the plunger tip, which could result in uneven pressure on the plunger tip during use of the syringe.

Therefore, it is desirable to have a plunger tip that is not completely made of an elastomeric material, replacing at least some of the elastomeric material with another material, such as an inert polymeric material. In this way, the amount of surface area of the elastomeric material in contact with the contents of the syringe is reduced, leading to less potential breakdown of the plunger tip and less potential contamination of the syringe contents. Also, it is desirable to have such a plunger tip that reduces the amount of elastomeric material in contact with the inner wall of the syringe barrel to reduce the amount of "setting" of the elastomeric material and, in turn, reduce the amount of force required to begin movement of the plunger tip within the syringe barrel. Lastly, it is desirable to use a more rigid material within the plunger tip in order to provide a more rigid connection between the plunger and the plunger tip, thereby reducing the likelihood of misalignment of the plunger tip and plunger, leading to the exertion of uneven pressure on a loose plunger tip.

BRIEF SUMMARY OF THE INVENTION

Briefly stated, the invention is directed to a plunger tip for being located on a distal end of a syringe plunger. The plunger tip is in sliding sealed engagement with an interior surface of a syringe barrel. The interior surface of the syringe barrel has an interior diameter. The plunger tip includes a core constructed of a generally rigid material, for being secured to the distal end of the plunger. A series of circumferential ridges extends around and radially outwardly from the core. The ridges are made of elastomeric material. An external diameter of the ridges is larger than the interior diameter of the syringe barrel such that only the ridges of the plunger tip are in contact with the interior surface when the plunger tip is slidably engaged with the interior surface.

In another aspect, the invention is directed to a plunger tip for being located on a distal end of a syringe plunger. The plunger tip is in sliding sealed engagement with an interior surface of a syringe barrel. The plunger tip includes a core having a first end for being secured to the plunger, a second end opposite from said first end, and an endless sidewall between the first and second ends. The core is constructed of a generally rigid material. An elastomeric sleeve surrounds the endless sidewall such that the second end of the core is exposed.

In another aspect, the invention is directed to a combination syringe plunger and plunger tip for sliding sealed engagement with an interior surface of a syringe barrel. The interior surface of the syringe barrel having an interior diameter. The syringe plunger has a proximal end for the application of a force and a distal end for being positioned within the syringe barrel. The plunger tip is located on a distal end of the syringe plunger for sliding sealed engagement with the interior surface of the syringe barrel. The plunger tip includes a core secured to the distal end of the syringe plunger and is constructed of a generally rigid material. A series of circumferential ridges extend around and radially outwardly from the core. The ridges are made of elastomeric material. The external diameter of the ridges is larger than the interior diameter of the syringe barrel such that only the ridges of the plunger tip are in contact with the interior surface when the plunger tip is slidably engaged with the interior surface.

In another aspect, the invention is directed to a combination syringe plunger and plunger tip for sliding sealed engagement with an interior surface of a syringe barrel. The interior surface of the syringe barrel having an interior diameter. The syringe plunger has a proximal end for the application of a force and a distal end for being positioned within a syringe barrel. The plunger tip is located on a distal end of the syringe plunger for sliding sealed engagement with the interior surface of the syringe barrel. The plunger tip includes a core constructed of a generally rigid material. The core has a first end for being secured to the syringe plunger, a second end opposite from said first end, and an endless sidewall between the first and second ends. The plunger tip also includes an elastomeric sleeve surrounding the endless sidewall such that the second end of the core is exposed.

In another aspect, the invention is directed to a plunger tip for being urged by an actuator rod and for sliding sealed engagement with an interior surface of a syringe barrel. The plunger tip has a first flanged end, a second flanged end opposite from said first flanged end, and an endless sidewall between the first and second flanged ends. The plunger tip is constructed of a generally rigid material. An elastomeric sleeve is provided that surrounds the endless sidewall such that the elastomeric sleeve abuts the first and second flanged ends.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
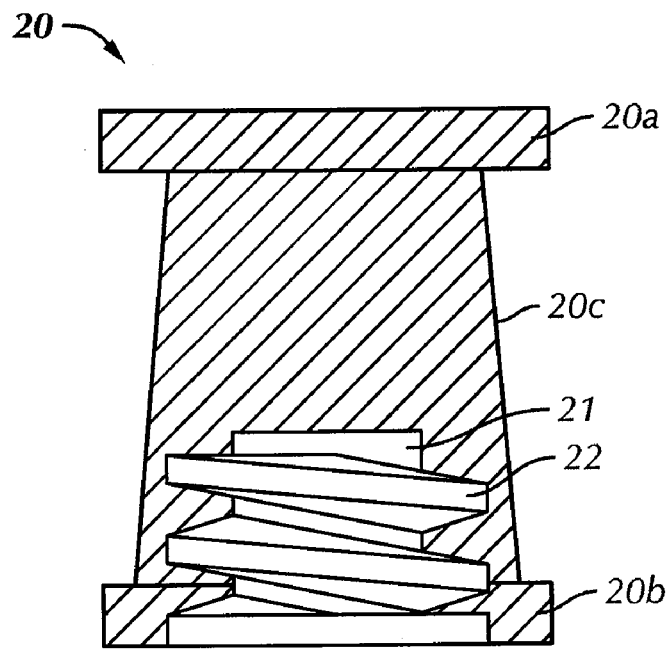
FIG. 1 is an enlarged cross-sectional side elevational view of a core for a plunger tip in accordance with a first embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of a plunger tip in accordance with the present invention, and designated parts thereof. The terminology includes the words noted above, derivatives thereof and words of similar import.

Referring to the drawings in detail, wherein like numerals indicate like elements throughout, there is shown in FIGS. 1, 6 and 12-15 a first embodiment of a plunger tip, indicated generally at 10, in accordance with the present invention. The plunger tip 10 has a core 20 engaged with an elastomeric sleeve 30. The core 20 is preferably made of a generally rigid material, such as a polymer and, more particularly, a medical grade polypropylene, for instance. The elastomeric sleeve 30 is preferably made of an elastomeric material (either a thermoplastic elastomer or a thermoset elastomer) having a Shore A hardness of between 30 and 80, and preferably between 40 and 70. Although these materials are preferred, it is within the spirit and scope of the present invention that the core 20 and elastomeric sleeve 30 be made of different materials, provided they are capable of performing as described herein. The plunger tip 10 is preferably co-injection molded, such that the core 20 is injection molded first, and then the elastomeric sleeve 30 is injection molded onto the premolded core 20. Although this is preferred, it is within the spirit and scope of the present invention that the plunger tip 10 be formed using another process, such molding the core 20 and elastomeric sleeve 30 separately and then assembling the plunger tip 10 thereafter, for instance.

Figure 6:
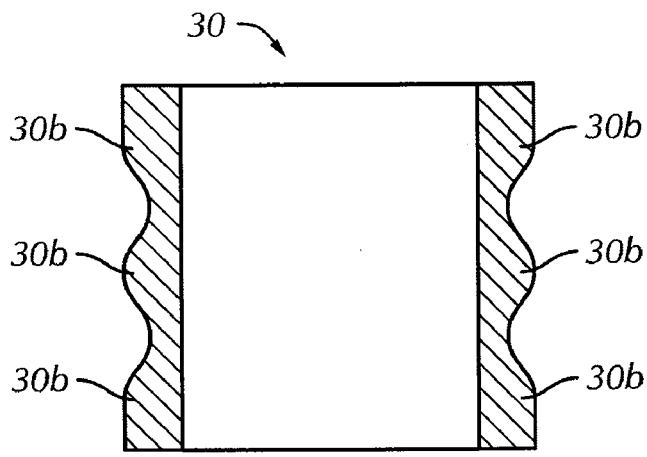
FIG. 6 is an enlarged cross-sectional view of an elastomeric sleeve for use with any of the cores in FIGS. 1-4.
Figure 7:
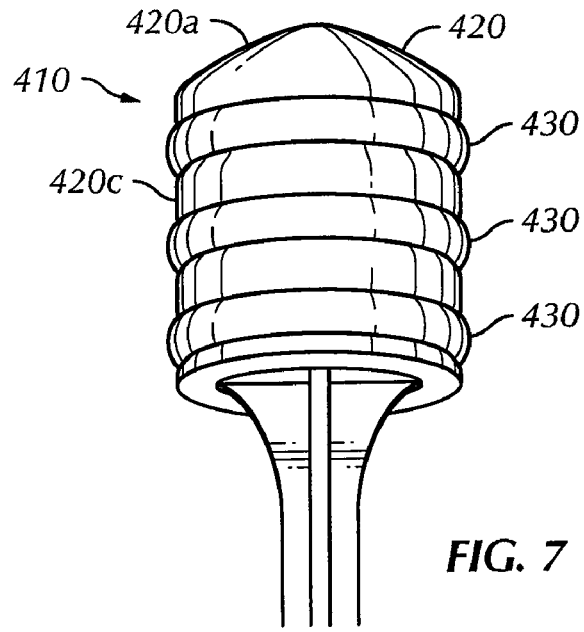
FIG. 7 is a partial side perspective view of a plunger tip and plunger in accordance with a fifth preferred embodiment of the present invention.
Figure 8:
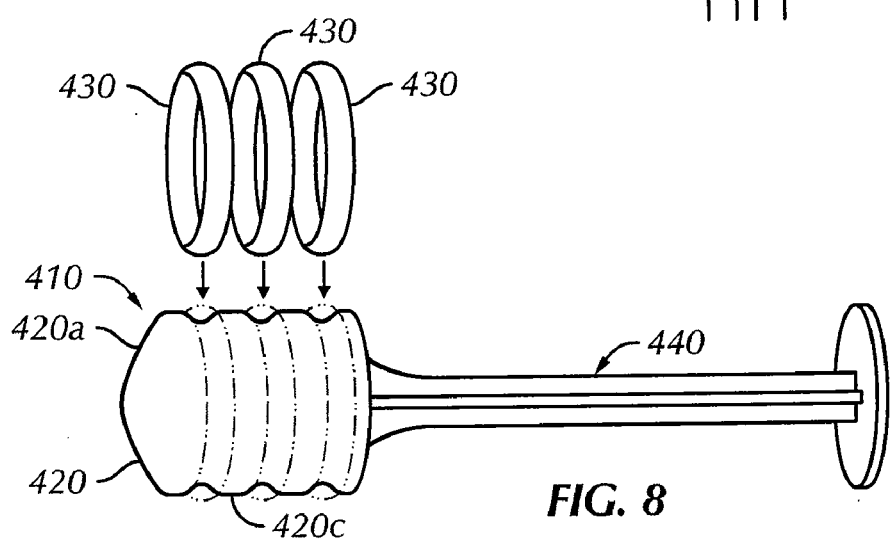
FIG. 8 is a side perspective view of the plunger tip and plunger of FIG. 7, having ridges removed from a core.
Figure 9:
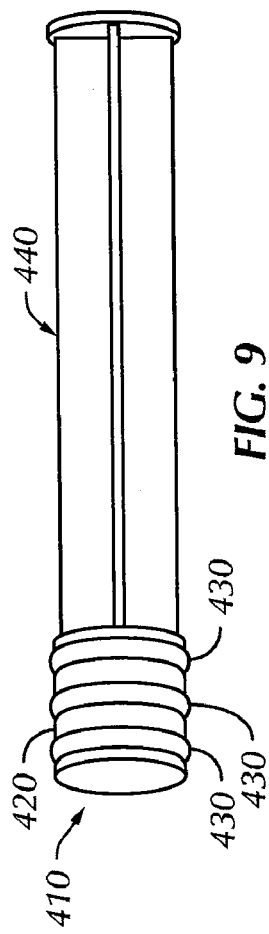
FIG. 9 is a side perspective view of the plunger tip and plunger of FIG. 8.
Figure 10:
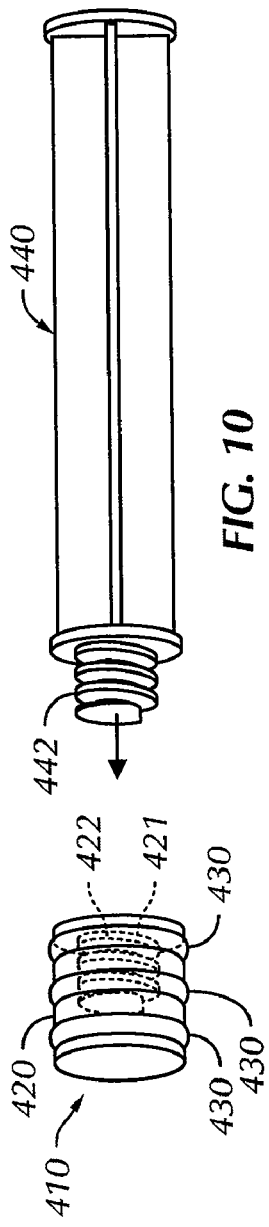
FIG. 10 is an exploded side perspective view of the plunger tip and plunger of FIG. 8.
Figure 13:
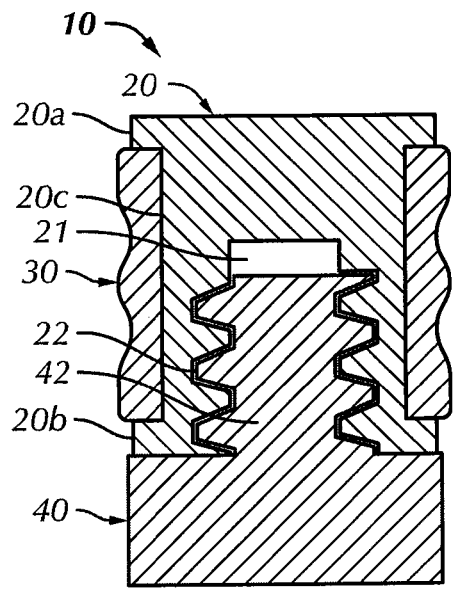
FIG. 13 is a cross-sectional view of the core, elastomeric sleeve, and plunger of FIG. 12 taken along line 13-13 of FIG. 12.
Figure 14:
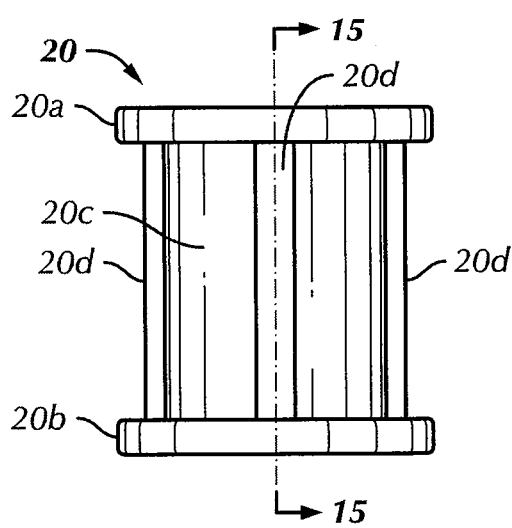
FIG. 14 is a side perspective view of the core of FIG. 12.
Figure 15:
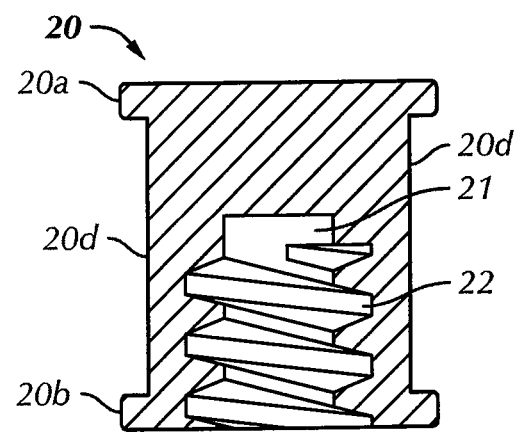
FIG. 15 is a cross-sectional view of the core of FIG. 14 taken along line 15-15 of FIG. 14.
Figure 16:
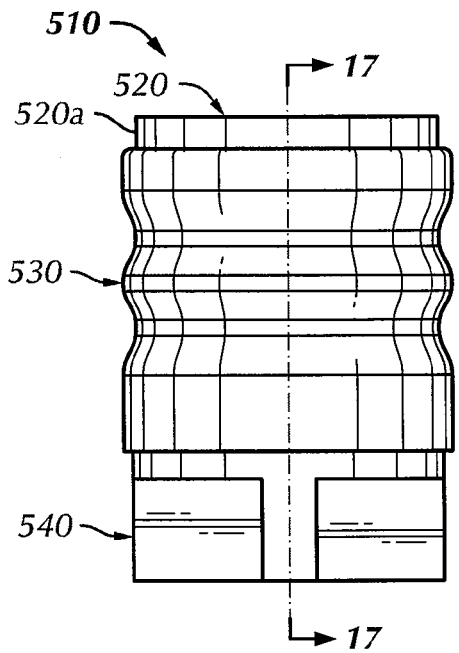
FIG. 16 is an enlarged side perspective view of a plunger tip and plunger in accordance with a sixth embodiment of the present invention.
Figure 17:
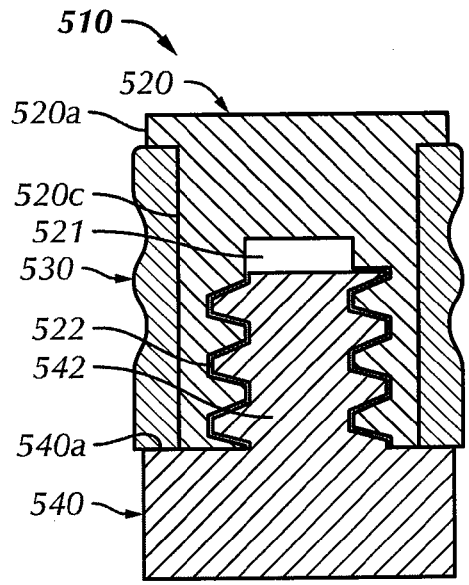
FIG. 17 is a cross-sectional view of the plunger tip and plunger of FIG. 16.
Figure 18:
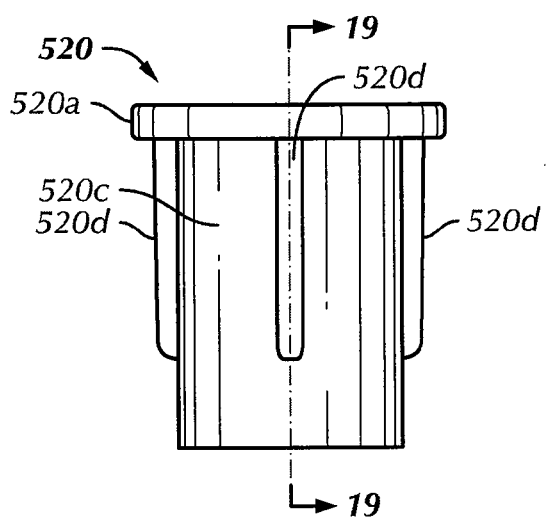
FIG. 18 is a side perspective view of a core of the plunger tip of FIG. 16.
Figure 19:
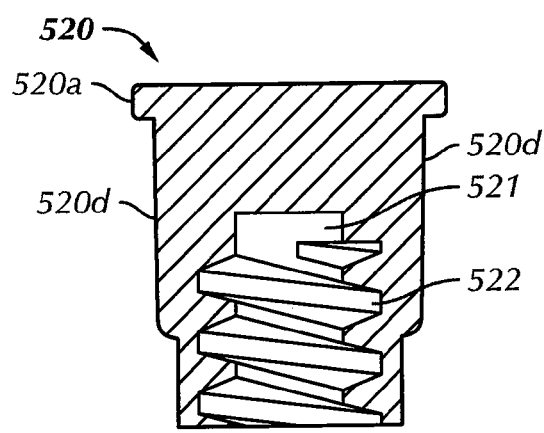
FIG. 19 is a cross-sectional view of the core of FIG. 18 taken along line 19-19 of FIG. 18.
Figure 20:
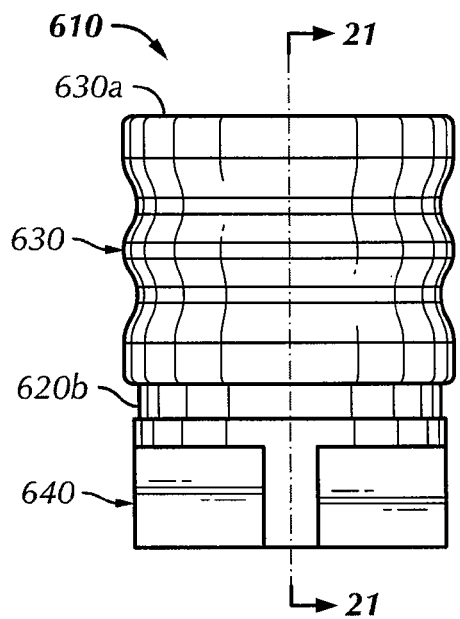
FIG. 20 is an enlarged side perspective view of a plunger tip and plunger in accordance with a seventh embodiment of the present invention.
Figure 21:
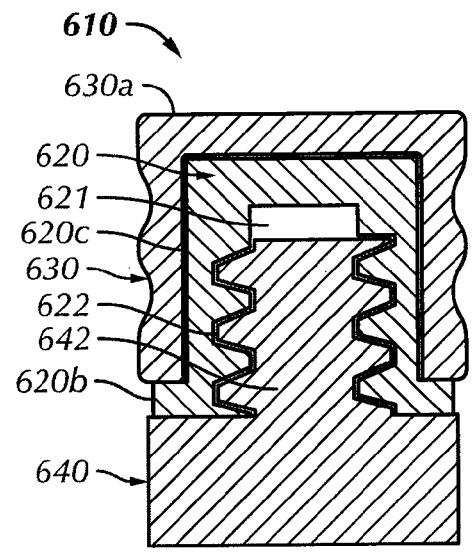
FIG. 21 is a cross-sectional view of the plunger tip and plunger of FIG. 20 taken along line 21-21 of FIG. 20.
Figure 22:
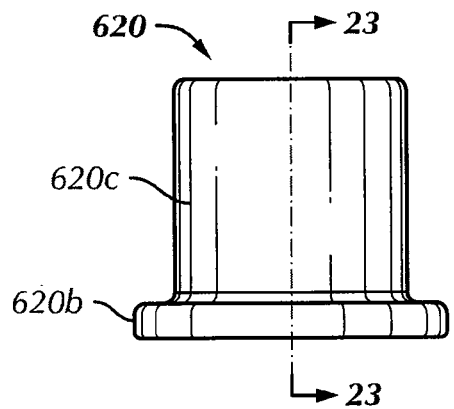
FIG. 22 is a side elevational view of a core of the plunger tip of FIG. 20.
Figure 23:
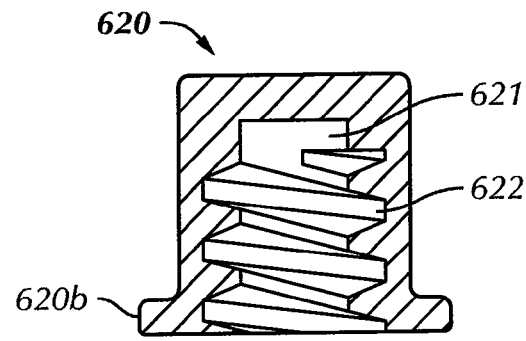
FIG. 23 is a cross-sectional view of the core of FIG. 22 taken along line 23-23 of FIG. 22.
Figure 24:
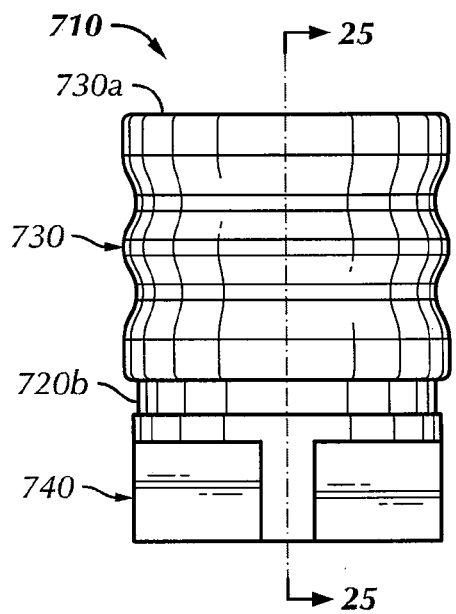
FIG. 24 is an enlarged side perspective view of a plunger tip and plunger in accordance with an eighth embodiment of the present invention.
Figure 25:
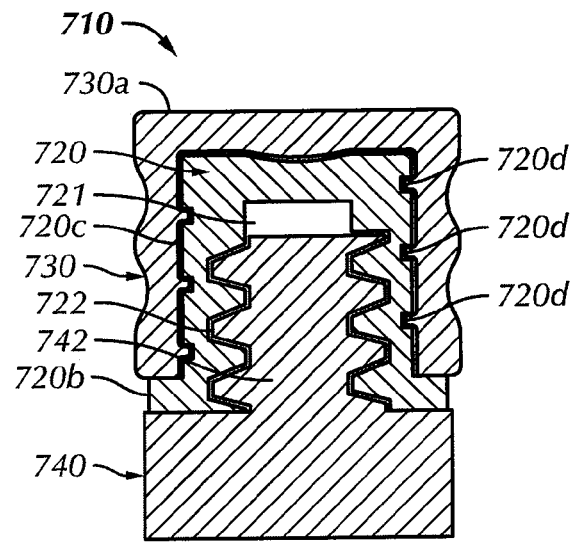
FIG. 25 is a cross-sectional view of the plunger tip and plunger of FIG. 24 taken along line 25-25 of FIG. 24.
Figure 26:
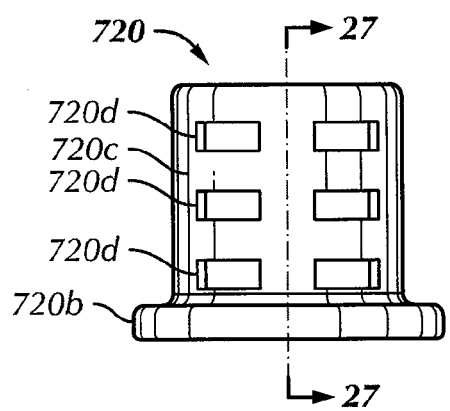
FIG. 26 is a side perspective view of a core of the plunger tip of FIG. 24.
Figure 27:
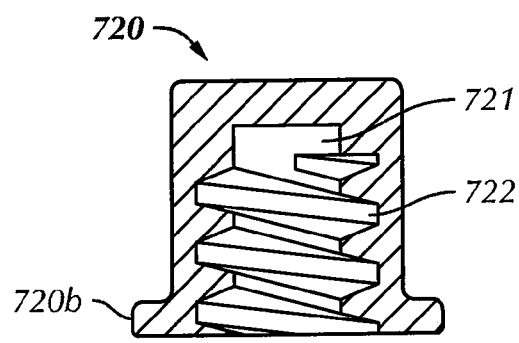
FIG. 27 is a cross-sectional view of the core of FIG. 26 taken along line 27-27 of FIG. 26.
Figure 28:
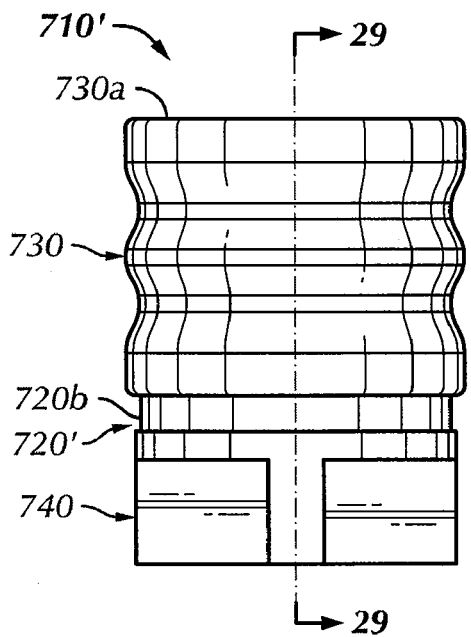
FIG. 28 is an enlarged side elevational view of a plunger tip in accordance with a ninth embodiment of the present invention.
Figure 29:
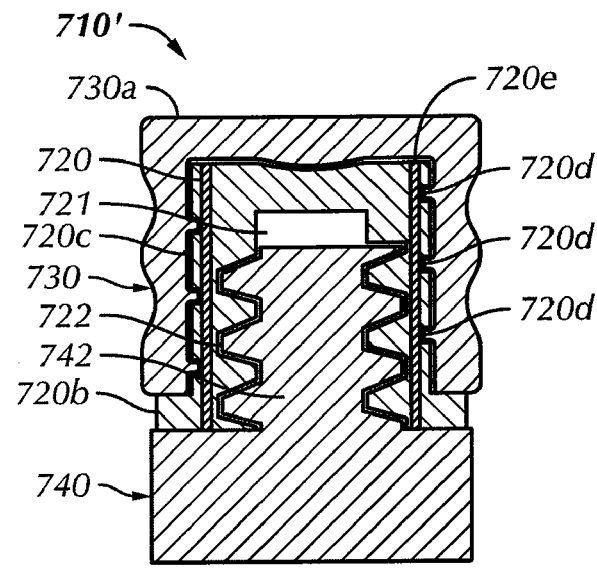
FIG. 29 is a cross-sectional view of the plunger tip and plunger of FIG. 28 taken along line 29-29 of FIG. 28.
Figure 30:
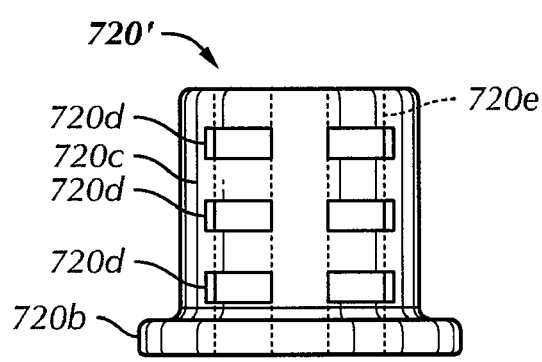
FIG. 30 is a side perspective view of a core of the plunger tip of FIG. 28.
Figure 31:
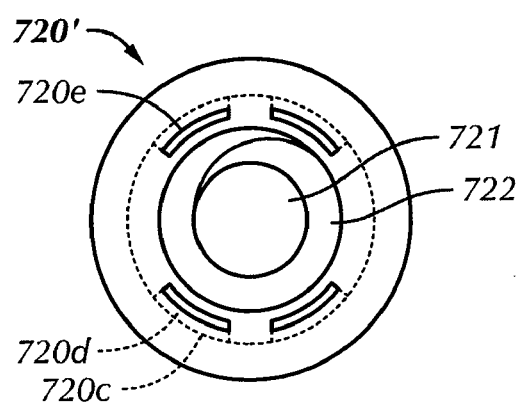
FIG. 31 is a bottom plan view of the core of FIG. 30.

Referring to FIGS. 6 and 13, the elastomeric sleeve 30 is generally tubular having an open bottom and top. The sleeve 30 has a series of circumferential ridges 30b that extend around and radially outward therefrom. Preferably, the elastomeric sleeve 30 has three circumferential ridges 30b, although it is within the spirit and scope of the present invention that there be more or less than three ridges 30b.

Referring again to FIGS. 1, 14, and 15, the core 20 is generally cylindrical in shape, having a generally cylindrical endless sidewall 20c with a circular flanged first end 20b extending outwardly from a bottom thereof and an opposite circular flanged second end 20a extending outwardly from a top thereof. The endless sidewall 20c extends between the first and second ends 20b, 20a. Although described as generally cylindrical, the sidewall 20c may have a slight inward slant from the first end 20b to the second end 20a, as shown slightly exaggerated in FIG. 1. It is further preferable that the sidewall 20c have axially extended ridges 20d extending slightly radially outwardly from the sidewall 20c. Preferably, there are four evenly-spaced ridges 20d extending axially along the sidewall 20c, although it is within the spirit and scope of the present invention that there be more or less than four ridges 20d. The elastomeric sleeve 30 surrounds the endless sidewall 20c such that the second end 20a of the core 20 is exposed. Disposed within the core 20 is a bore 21 extending at least partially therethrough. Formed in a sidewall of the bore 21 is a female thread 22.

Figure 12:
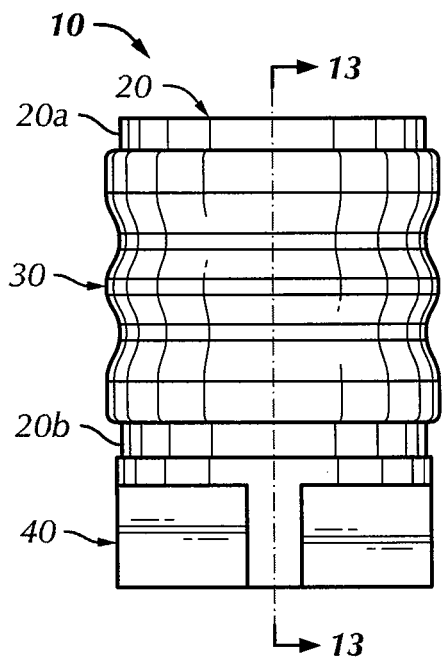
FIG. 12 is an enlarged side elevational view of the core of FIG. 1, having an elastomeric sleeve and a plunger attached thereto.

Referring specifically to FIGS. 12 and 13, the first end 20b of the core 20 is attached to the distal end of a plunger 40 having male threads 42 that threadably engage with the female threads 22 of the core 20. The elastomeric sleeve 30 is preferably disposed between the first and second ends 20b, 20a, such that it surrounds the sidewall 20c of the core 20. In this way, the elastomeric sleeve 30 is retained on the core 20 between the first and second ends 20b, 20a. The ridges 20d aid in engagement of the elastomeric sleeve 30 with the core 20 by providing disruptions in the otherwise smooth surface of the sidewall 20c, thereby reducing the likelihood of rotation of the elastomeric sleeve 30 with respect to the core 20. Also, the slight slant to the sidewall 20c of the core 20 reduces the likelihood of the elastomeric sleeve 30 moving axially downwardly, towards the plunger, and compressing against the first end 20b during use of the plunger tip 10.

Figure 11:
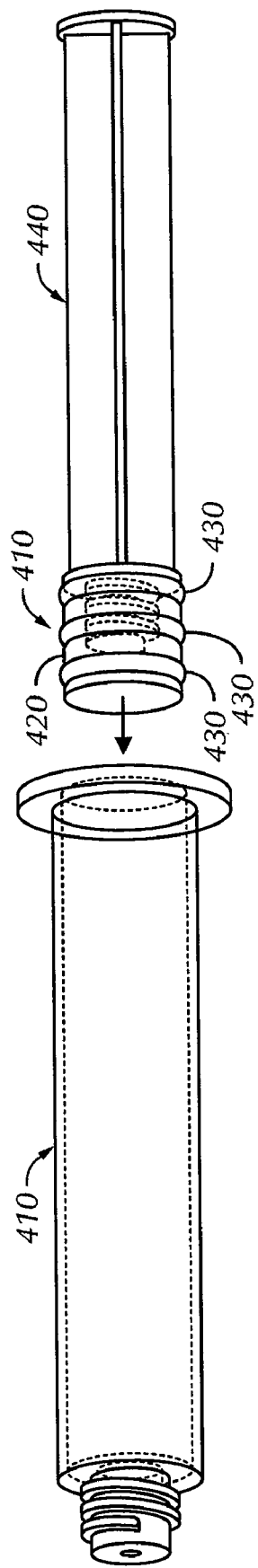
FIG. 11 is a side perspective view of the plunger tip and plunger of FIG. 8 and a conventional syringe barrel.

In use, the plunger tip 10 is either co-molded or separately molded and assembled. The plunger tip 10 is then threadably engaged with the distal end of the plunger 40. The distal end of the plunger 40 including the plunger tip 10 can then be inserted within a conventional syringe barrel 400 (see FIG. 11). A user then applies a force to the proximal end of the plunger 40 to urge the contents (not shown) out from within the syringe barrel 400. The external diameter of the ridges 30b is larger than the interior diameter of the syringe barrel 400 such that the ridges 30b of the elastomeric sleeve 30 are compressed between the core 20 and an interior surface of the syringe barrel 400 to create a sliding sealed engagement, thereby preventing the contents of the syringe barrel 400 from escaping from the syringe barrel between the plunger tip 10 and the interior surface of the syringe barrel 400.

Figure 2:
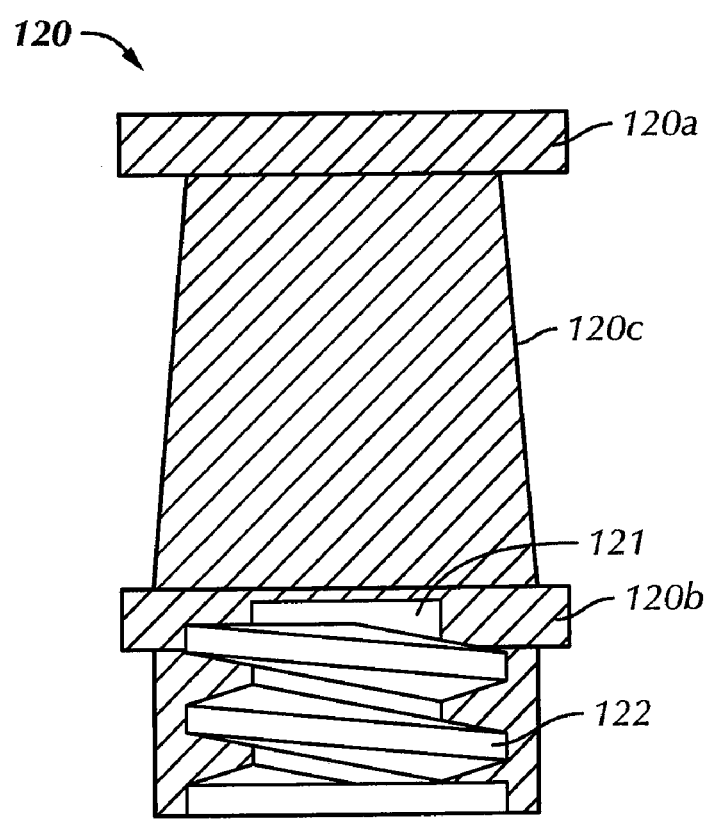
FIG. 2 is an enlarged cross-sectional side elevational view of a core of a plunger tip in accordance with a second embodiment of the present invention.

Referring to FIG. 2, there is shown a core 120 in accordance with a second embodiment of the present invention. The core 120 of the second embodiment is similar to the core 20 of the first embodiment, except that the core 120 has an extension 120e extending downwardly from a bottom flange 120b. The extension 120e allows the core 120 to accommodate threads 122 within a bore 121 which are wider than a diameter of a sidewall 120c of the core 120. In this way, if it is desired that the sidewall 120c have a diameter that is smaller than a diameter of the threads 122, the wider threads 122 can be accommodated within the extension 120e of the core 120. In this way, the wider diameter threads 122 can be contained entirely within the core 120, and no threads 122 become exposed through the sidewall 120c.

Figure 3:
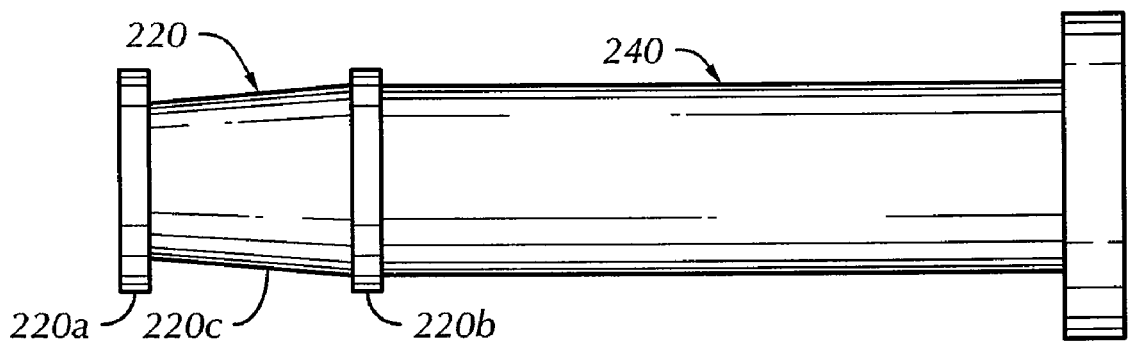
FIG. 3 is an enlarged side elevational view of a combined core and plunger in accordance with a third embodiment of the present invention.

Referring to FIG. 3, there is shown a core 220 in accordance with a third embodiment of the present invention. The core 220 is similar to the core 20 of the first embodiment, except that the core 220 is integrally molded with a plunger 240, rather than being threadably engaged therewith. In this way, the core 220 and the plunger 240 can be molded together and, consequently, do not require additional assembly time to attach the core 220 to the plunger 240 subsequently, thereby decreasing the time and cost of assembly.

Figure 4:
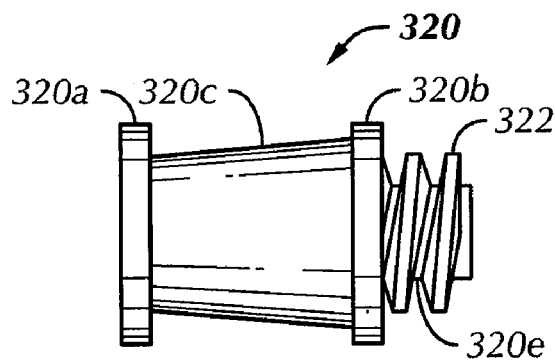
FIG. 4 is an enlarged side elevational view of a core of a plunger tip in accordance with a fourth embodiment of the present invention.
Figure 5:
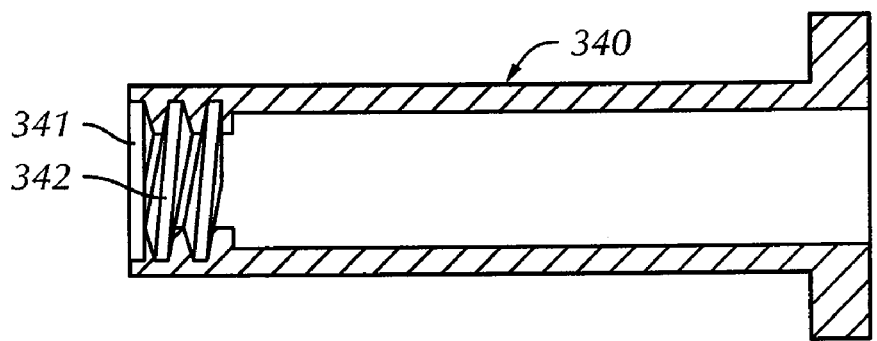
FIG. 5 is a cross-sectional view of a plunger for use with the core of FIG. 4.

Referring to FIGS. 4 and 5, there is shown a core 320 in accordance with a fourth embodiment of the present invention. The core 320 is similar to the core 20 of the first embodiment, except that, instead of female threads disposed within a bore of the core 320, the core 320 has male threads 322 extending outwardly from an extension 320e extending downwardly from a bottom of a bottom flange 320b. The threads 322 of the core 320 engage with female threads 342 of a plunger 340 disposed within a bore 341 that extends at least partially through the plunger 340.

Preferably, each of the above-described cores 20, 120, 220, 320 of the first four embodiments are designed to accept an elastomeric sleeve 30 of the type shown in FIGS. 6 and 13. As stated above, the elastomeric sleeve 30 is preferably co-molded with the cores 20, 120, 220, 320, although it is contemplated that the elastomeric sleeve 30 be molded separately from the cores 20, 120, 220, 320 and then subsequently attached to the cores 20, 120, 220, 320.

Referring to FIGS. 7-11, there is shown a plunger tip 410 in accordance with a fifth embodiment of the present invention. The plunger tip 410 has a polymeric core 420 having a generally circular, slightly pointed tip 420a and a generally cylindrical sidewall 420c extending downwardly therefrom. The core 420 is preferably constructed of a polymeric material but it may be constructed of any generally rigid materials similar to the core 20 of the first embodiment. Although shown with a pointed tip 420a, it is within the spirit and scope of the present invention that the plunger tip 420 have a second end similar to 20a of the first embodiment. Disposed around the sidewall 420c are three generally equally, axially spaced, and radially extending circumferential rings 430, rather than the sleeve 30 of the previously-described embodiments of the present invention. Although shown with three rings 430, it is within the spirit and scope of the present invention that the plunger tip 420 have more or less than three rings 430 disposed along the sidewall 420c of the core 420. The plunger tip 410 is secured to the distal end of a plunger 440. The plunger 440 can be either integrally molded with the core 420 (like the core 220 and plunger 240 of the third embodiment) or threadably engaged with the core 420 with threads 442 of the plunger 440 engaging with threads 422 within a bore 421 of the core 420 (like the core 20 and plunger 40 of the first embodiment). The assembled plunger tip 410 and plunger 440 can then be used within a syringe barrel 400 in order to urge the syringe contents (not shown) from within the syringe barrel 400. The rings 430 providing a sliding seal between the core 420 and an interior surface of the syringe barrel 400 to inhibit the contents from leaking from the syringe barrel 400.

Referring to FIGS. 16-19, a plunger tip 510 in accordance with a sixth embodiment of the present invention is shown. The plunger tip 510 is similar to the plunger tip 10 of the first embodiment, except that a core 520 has no bottom flange, the core 520 having only a top flange 520a with a generally cylindrical sidewall 520c extending downwardly therefrom. As with the first embodiment, the core 520 preferably has axially extending ridges 520d extending slightly outwardly from the sidewall 520c. The lack of a bottom flange allows an elastomeric sleeve 530 to be more easily placed on the core 520, if the core 520 and elastomeric sleeve 530 are molded separately. The plunger tip 510 can then be threadably engaged or otherwise attached to a plunger 540, such that a top end 540a of the plunger 540 abuts a bottom of the elastomeric sleeve 530 to act as a bottom flange, thereby preventing the elastomeric sleeve 530 from sliding axially downwardly along the sidewall 520c and retaining the elastomeric sleeve 530 on the core 520 during use of the plunger tip 510 and plunger 540.

Referring to FIGS. 20-23, there is shown a plunger tip 610 in accordance with a seventh embodiment of the present invention. The plunger tip 610 is similar to the plunger tip 10 of the first embodiment, except that there is no top flange extending from a top of the core 620, the core 620 having only a bottom flange at a first end 620b. Also, a sidewall 620c of the core 620 is essentially smooth and has no ridges. This configuration allows an elastomeric sleeve 630 to be attached to the core 620 by sliding the elastomeric sleeve 630 over the top of the core 620 if the core 620 and the sleeve 630 are molded separately. The elastomeric sleeve 630 has a top surface 630a that surrounds a second end of the core 620 when engaged therewith. Although not reducing the amount of elastomeric material in contact with the contents of the syringe barrel, the core 620 still allows for a relatively rigid connection to be formed between the core 620 and a plunger 640, thereby decreasing the likelihood of misalignment of the plunger tip 610 and the plunger 640 during use.

Referring to FIGS. 24-27, a plunger tip 710 in accordance with an eighth embodiment of the present invention is shown. The plunger tip 710 of the eighth embodiment is similar to the plunger tip 610 of the seventh embodiment, except that a sidewall 720c of a core 720 of the plunger tip 710 has a plurality of generally rectangularly-shaped depressions 720d therein. Although shown as generally rectangularly shaped, it is within the spirit and scope of the present invention that the depressions 720d have different shapes, such as circular, triangular, or the like. The depressions 720d allow for enhanced engagement between the core 720 and an elastomeric sleeve 730 by allowing elastomeric material of the elastomeric sleeve 730 to be disposed within the depressions 720d during co-molding of the plunger tip 710. Because the elastomeric sleeve 730 is partially disposed within the depressions 720d, there is less likelihood that the elastomeric sleeve 730 will rotate or move axially with respect to the core 720 during use.

Referring to FIGS. 28-31, a plunger tip 710' in accordance with a ninth embodiment of the present invention is shown. The plunger tip 710' of the ninth embodiment is similar to the plunger tip 710 of the eighth embodiment, except a plurality of core slots 720e extend axially through the core 720'. The core slots 720e are in communication with the depressions 720d allowing for even further enhanced engagement between the core 720' and an elastomeric sleeve 730 by allowing elastomeric material of the elastomeric sleeve 730 to be disposed within the depressions 720d and through the core slots 720e during co-molding of the plunger tip 710. Because the elastomeric sleeve 730 is partially disposed within the depressions 720d and the core slots 720e, substantially preventing the elastomeric sleeve 730 from rotating or moving axially with respect to the core 720' during use. The core slots 720e may be part of the molding of the core 720' or subsequently added to the core 720 by drilling through the top or the bottom of the core 720. Though the core slots 720e are shown as extending through the entire core 720, it is within the spirit and scope of the present invention that the core slots 720 extend only partially through the core 720 from one end of the core 720. It is also within the spirit and scope of the invention that core slots 720e have different cross sectional shapes, such as circular, triangular, or the like.

Figure 32:
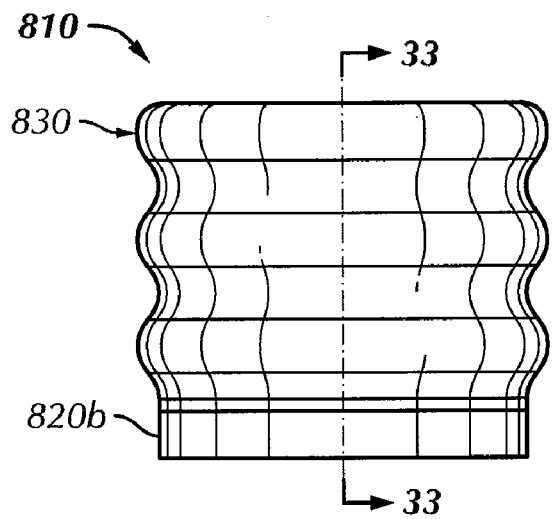
FIG. 32 is an enlarged side elevational view of a plunger tip in accordance with a tenth embodiment of the present invention.
Figure 33:
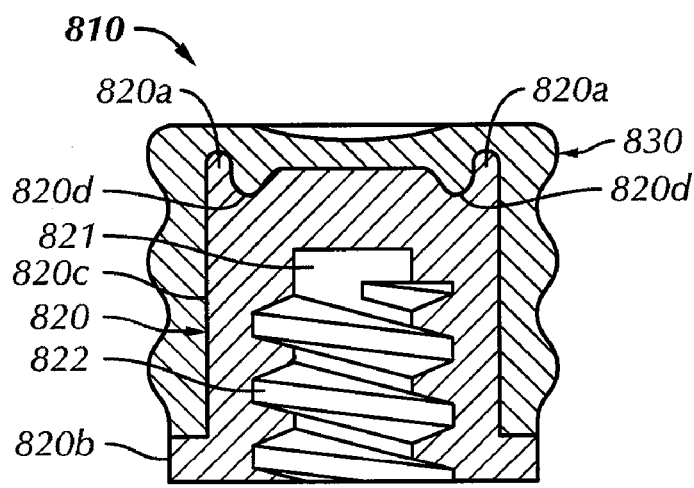
FIG. 33 is a cross-sectional view of the plunger tip of FIG. 32 taken along line 33-33 of FIG. 32.
Figure 34:
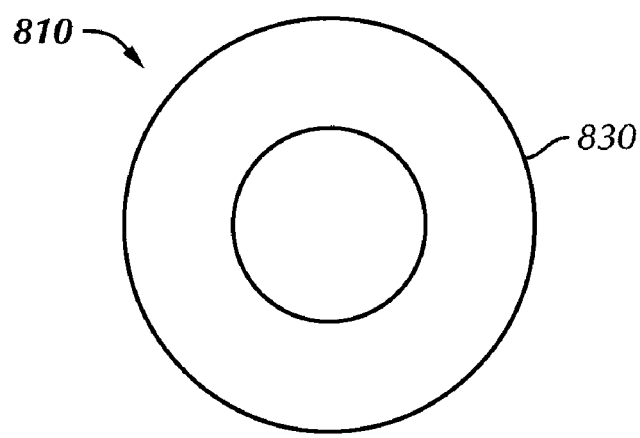
FIG. 34 is a top plan view of the plunger tip of FIG. 32.

Referring to FIGS. 32-34, a plunger tip 810 in accordance with a tenth embodiment of the present invention is shown. The plunger tip 810 of the tenth embodiment is similar to the plunger tip 610 of the seventh embodiment, except that a top of a core 820 of the plunger tip 810 has a generally annular protrusion 820a extending outwardly from a second end of the core 820. Although it is preferred that the annular protrusion 820a form a continuous ring, it is within the spirit and scope of the present invention that the annular protrusion 820a be segmented. An annular channel 820d is preferably disposed in the second end of the core 820 inwardly of the annular protrusion 820a. Although it is preferred that the annular channel 820d is continuous, it is within the spirit and scope of the present invention that the annular channel 820d be segmented. Also, although portrayed proximate the annular protrusion 820a, it is within the spirit and scope of the present invention that the annular channel 820d be located anywhere along the top or second end of the core 820. The annular protrusion and channel 820a, 820d allow for enhanced engagement between the core 820 and a sleeve 830 by allowing elastomeric material of the elastomeric sleeve 830 to be disposed within the annular channel 820d and around the annular protrusion 820a during co-molding of the plunger tip 810. Because the elastomeric sleeve 830 is partially disposed within the annular channel 820d, there is less likelihood that the elastomeric sleeve 830 will move with respect to the core 820 during use.

Figure 35:
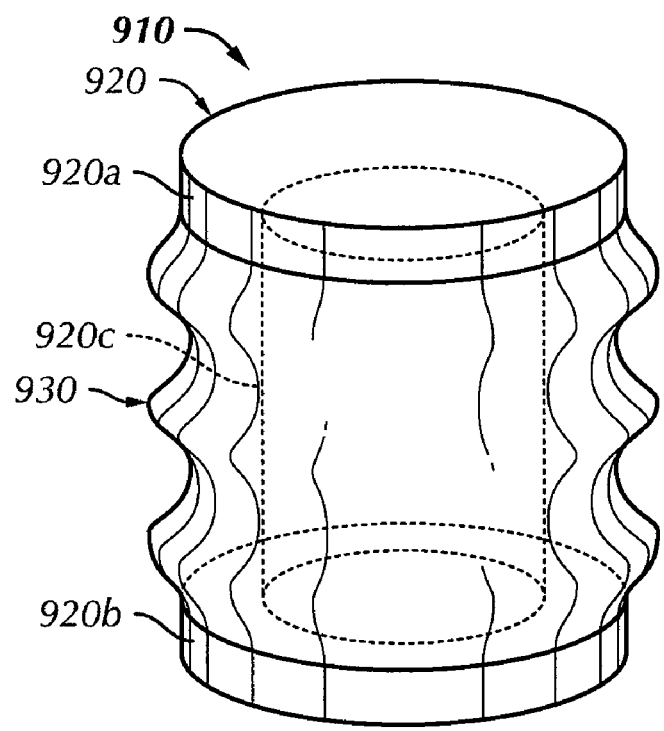
FIG. 35 is an enlarged side perspective view of a plunger tip in accordance with an eleventh embodiment of the present invention.
Figure 36:
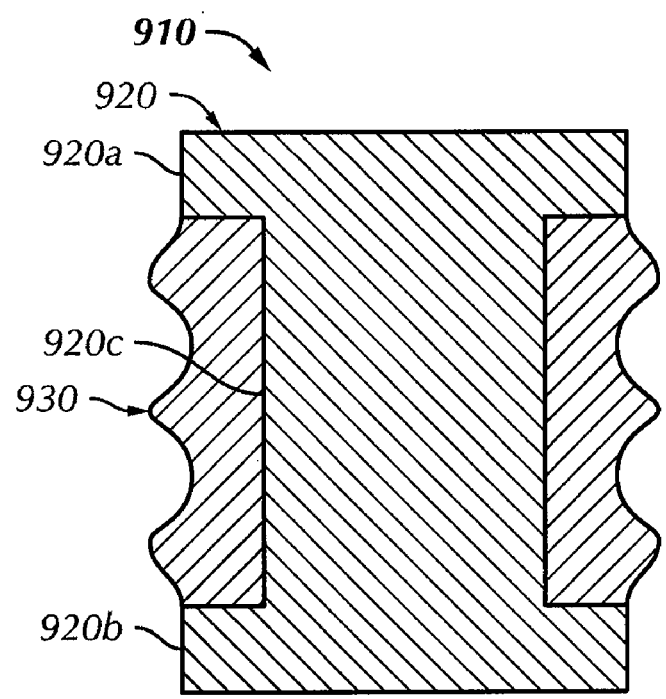
FIG. 36 is a side cross-sectional view of the plunger tip of FIG. 35

Referring to FIGS. 35 and 36, a plunger tip 910 in accordance with an eleventh embodiment of the present invention is shown. In certain applications, such as automatic dosing systems (not shown), for instance, it is desirable to have no plunger attached to the plunger tip 910, thereby allowing a core 920 of the plunger tip 910 to have generally solid top and bottom flanged ends 920a, 920b. That is, neither the top nor the bottom flanged ends 920a, 920b have a hole therein to allow a plunger to be threadably attached or otherwise fixedly engaged with the plunger tip 910. Instead, the plunger tip 910 is preferably intended to be used with an actuator rod (not shown), an end of which abuts and pushes against one of the top and bottom flanged ends 920a, 920b in order to move the plunger tip 910 within the syringe barrel. An elastomeric sleeve 930 is disposed on the generally rigid core 920, preferably between the top and bottom flanged ends 920a, 920b. Although the core 920 is portrayed as being smooth, it is within the spirit and scope of the present invention that the core 920 have ridges, depressions, or other similar structures, similar to those described above, to aid in retaining the elastomeric sleeve 930 on the core 920 and inhibiting rotation and/or axial movement of the elastomeric sleeve 930 with respect to the core 920. Furthermore, although it is preferred that the core 920 have top and bottom flanged ends 920a, 920b, it is within the spirit and scope of the present invention that either or both of the ends 920a, 920b have no flange extending therefrom, thereby enabling a sleeve to have a shape similar to the elastomeric sleeve 730 of the eighth embodiment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

We claim:

1. A plunger tip for being urged by an actuator rod and for sliding sealed engagement with an interior surface of a syringe barrel, said plunger tip comprising:

a core for being secured to the distal end of the plunger and having a first flanged end, a second flanged end opposite from said first flanged end and an endless sidewall extending between the first and second flanged ends, the sidewall having a minimum diameter, the core being constructed of a generally rigid material, threads proximate the sidewall and having a maximum diameter, the maximum diameter of the threads being larger than the minimum diameter of the sidewall; and an elastomeric sleeve surrounding the endless sidewall such that the sleeve abuts the first and second flanged ends and such that the first and second flanged ends are at least partially exposed.

2. The plunger tip of claim 1, wherein the threads are female threads extending into the core for being secured onto male threads on the plunger.

3. The plunger tip of claim 1, wherein the core further includes an extension extending axially from the first flanged end of the core and containing the threads.

4. The plunger tip of claim 1, wherein the threads are male threads extending axially from the first flanged end of the core.

5. The plunger tip of claim 1, wherein the sidewall has a plurality of depressions for enhanced retention of the sleeve.

6. A plunger tip for being located on a distal end of a syringe plunger and for sliding sealed engagement with an interior surface of a syringe barrel, the interior surface of the syringe barrel having an interior diameter, said plunger tip comprising:

a core for being secured to the distal end of the plunger, the core having
a first end for being secured to the plunger,
a second end opposite from said first end, and
an endless sidewall between the first and second ends, the first end of the core includes a radially extending first flange, the core being constructed of a generally rigid material and including
a plurality of depressions and
a plurality of axially extending core slots in communication with the plurality of depressions; and an elastomeric sleeve having a series of circumferential ridges extending around and radially outwardly from said sleeve, wherein an external diameter of the ridges is larger than the interior diameter of the syringe barrel such that only the ridges of the plunger tip are in contact with the interior surface when the plunger tip is slidably engaged with the interior surface, the sleeve surrounding the endless sidewall and abutting the first flange such that second end of the core is exposed and wherein the sleeve at least partially fills the plurality of depressions and the plurality of core slots.

7. The plunger tip of claim 6, wherein the second end of the core is generally equal in diameter to the sidewall such that the sleeve slides over the second end during assembly and abuts the first flange and the distal end of the plunger when assembled.

8. The plunger tip of claim 6, wherein the second end of the core has a radially extending second flange such that the sleeve is disposed between the first and second flanges.

9. A plunger tip for being located on a distal end of a syringe plunger and for sliding sealed engagement with an interior surface of a syringe barrel, the interior surface of the syringe barrel having an interior diameter, said plunger tip comprising:

a core for being secured to the distal end of the plunger, the core having
a first end for being secured to the plunger,
a second end opposite from said first end,
an endless sidewall between the first and second ends, the core being constructed of a generally rigid material; and
a plurality of circumferential axially spaced depressions disposed around the endless sidewall; and a plurality of independent elastomeric rings which are axially spaced and are disposed about the plurality of circumferential axially spaced depressions, an external diameter of each ring being larger than the interior diameter of the syringe barrel such that only the rings are in contact with the interior surface when the plunger tip is slidably engaged with the interior surface, the rings surrounding the endless sidewall of the core such that the second end of the core is exposed.

10. The plunger tip of claim 9, wherein the second end of the core forms a pointed tip.

11. The plunger tip of claim 1, wherein the sidewall includes a proximal diameter and a distal diameter, and wherein the proximal diameter is larger than the distal diameter.

12. The plunger tip of claim 6, wherein the plurality of depressions includes two depressions connected inside the core by the at least one core slot of the plurality of core slots.

* * * * *